United States Patent
Sultan et al.

(10) Patent No.: US 7,279,132 B2
(45) Date of Patent: Oct. 9, 2007

(54) CHEMICAL VAPOR SENSOR HAVING AN ACTIVE AND A PASSIVE MEASUREMENT MODE

(75) Inventors: Michel F. Sultan, Troy, MI (US); David K. Lambert, Sterling Heights, MI (US)

(73) Assignee: Delphi Technologies, Inc., Troy, MI (US)

( * ) Notice: Subject to any disclaimer, the term of this patent is extended or adjusted under 35 U.S.C. 154(b) by 90 days.

(21) Appl. No.: 11/033,703

(22) Filed: Jan. 12, 2005

(65) Prior Publication Data

US 2006/0153740 A1    Jul. 13, 2006

(51) Int. Cl.
B32B 5/02        (2006.01)
B32B 27/04       (2006.01)
B32B 27/12       (2006.01)
G01N 7/00        (2006.01)
G01N 21/00       (2006.01)

(52) U.S. Cl. .......................... 422/83; 422/84; 422/100; 422/101; 436/43; 436/164; 436/167; 436/171; 436/174; 436/178; 73/23.2; 73/23.3; 73/23.41; 73/23.42; 73/1.01; 73/1.02

(58) Field of Classification Search .......... 422/83, 422/84, 100, 101; 436/43, 164, 167, 171, 436/174, 178; 73/23.2, 23.3, 23.41, 23.42, 73/1.01, 1.02
See application file for complete search history.

(56) References Cited

U.S. PATENT DOCUMENTS

| | | | |
|---|---|---|---|
| 3,792,272 A * | 2/1974 | Harte et al. ................ 250/343 |
| 3,815,087 A | 6/1974 | Hirano et al. ................ 340/53 |
| 4,759,210 A * | 7/1988 | Wohltjen .................... 73/31.07 |
| 5,162,652 A * | 11/1992 | Cohen et al. ............... 250/288 |
| 5,907,407 A * | 5/1999 | Atkinson et al. .......... 356/437 |
| 6,174,732 B1* | 1/2001 | Ong et al. .................. 436/177 |
| 6,313,464 B1* | 11/2001 | Schrader ..................... 250/349 |
| 6,599,253 B1* | 7/2003 | Baum et al. ................ 600/532 |
| 7,095,501 B2* | 8/2006 | Lambert et al. ........... 356/439 |
| 2006/0154377 A1* | 7/2006 | Lambert et al. ............ 436/167 |

OTHER PUBLICATIONS

John McCormick, "Safety Steps," Supplier Technology/Safety, Automotive Industries, Dec. 2001.
U.S. Appl. No. 10/348,496, filed Jan. 21, 2003.

* cited by examiner

*Primary Examiner*—Brian Sines
(74) *Attorney, Agent, or Firm*—Jimmy L. Funke

(57) ABSTRACT

A chemical vapor sensor is provided that measures a chemical species of interest with high sensitivity and chemical specificity. In an aspect, an ethanol vapor sensor is provided, sized for being inconspicuous and on-board a vehicle, having a passive measurement mode and an active breathalyzer mode, for detecting a motor vehicle driver that exceeds a legal limit of blood alcohol concentration (BAC), for use with vehicle safety systems. For the passive mode, a vapor concentrator is utilized to amplify a sampled vapor concentration to a detectible level for use with an infrared (IR) detector. In an aspect, ethanol vapor in a vehicle cabin is passively measured and if a predetermined ethanol level is measured, a countermeasure is invoked to improve safety. In an aspect, an active breathalyzer is used as a countermeasure. The active breathalyzer can be imposed for a number of vehicle trips or for a predetermined time period.

11 Claims, 7 Drawing Sheets

CHEMICAL VAPOR SENSOR HAVING AN ACTIVE AND A PASSIVE MEASUREMENT MODE

FIELD OF THE INVENTION

The invention relates generally to a chemical vapor sensor, and more particularly to actively and passively measuring, with high sensitivity and chemical specificity, a chemical species of interest, for use with safety systems.

BACKGROUND OF THE INVENTION

Intoxicated drivers are a major cause of traffic accident fatalities in the United States. A recent NHTSA report showed that 40% of the total accident fatalities in the U.S. in the year 2003 were alcohol related. More specifically, 12,373 motor vehicle occupants were killed in crashes that involved a blood alcohol concentration (BAC) of 0.08% or higher. This equates to over 33% of the 37,132 U.S. motor vehicle fatalities in 2003. In addition to the societal impact, the cost of such crashes in the U.S. is about $40 billion per year. It is well established that the rate of fatal traffic accidents per mile traveled is related to a driver's (BAC) and that there is a correlation between impairment in driving skills and the driver's BAC. The definition of drunk driving in the U.S. involves a BAC level of either 0.08% or 0.10%, depending on the particular state law. Moreover, the states of the U.S. that currently have a 0.10% BAC limit have passed laws lowering the BAC limit to 0.08%, to take effect soon. A primary countermeasure to combat drunk driving in the U.S. is the criminal justice system, which employs deterrents and sanctions against drunk drivers. Various other approaches to combat drunk driving have been utilized. The following existing approaches require active involvement of a vehicle driver.

Ethanol concentration in human breath is a good indication of BAC. Inside the air sacs in the human lung, there is a chemical equilibrium between the concentration of ethanol in the air and the concentration of ethanol in an individual's blood. An approach to combat drunk driving, which utilizes this notion of ethanol concentration in human breath, uses an electrochemical sensor to measure ethanol concentration in air. For law enforcement purposes, an electrochemical sensor is built into an object such as a clipboard or flashlight that a police officer can, under certain circumstances, justifiably insert into a vehicle. However, currently available electrochemical sensors have a limited lifetime and typically must be replaced after about three years. To be used as an on-board component of the safety system, an ethanol sensor must have a lifetime of at least ten to fifteen years.

An additional approach to combat drunk driving uses a heated film of metal oxide that changes electrical resistance in response to ethanol concentration. Such sensors are used in commercially available "breath interlocks," sometimes mandated following a drunk driving conviction, which require the driver to breathe into a tube to check for excess breath alcohol before the vehicle will start. However, such sensors do not have sufficient sensitivity for passive detection of a drunk driver in regard to measuring ethanol vapor in the air of a vehicle cabin. The breath sample blown into a tube is undiluted so the detection level needed is only about 210 parts per million (ppm) ethanol, by volume. Also, the minimum ethanol concentration that can be reliably detected with a metal oxide film is typically in the range of 10 to 50 ppm. A further disadvantage is that the response to ethanol concentration is non-linear as a function of ethanol concentration.

A further approach to combat drunk driving uses an electrochemical sensor that is pressed against an individual's skin to determine alcohol intoxication through remote detection of ethanol that evaporates from the driver's skin. This approach is an active system since contact with the driver's skin is required. The lifetime of this sensor has not been demonstrated.

U.S. patents have been issued for approaches that combat drunk driving that involve passing infrared through one of the driver's extremities, such as a finger, or using Raman spectroscopy to measure the concentration of ethanol in the fluid at the surface of the driver's eyes (i.e., U.S. Pat. No. 6,574,501). These approaches are impractical for on-board vehicle use as well.

Further approaches to combat drunk driving exist. The following approaches are passive since active involvement of the driver is not required. For example, monitoring a vehicle driver's eyes to determine driver intoxication has been attempted. The direction of the driver's gaze is monitored as they visually follow a moving object. It is believed that an intoxicated person moves their gaze direction in jumps rather than following an object's motion smoothly and continuously.

A recently published patent application (U.S. patent application Ser. No. 20040141171, assigned to Delphi Technologies, Inc., filed Jan. 21, 2003) provides increased sensitivity with a short path length by using a vapor concentrator. Ethanol vapor is collected by passing air that contains ethanol vapor over an adsorber for a period of time. The adsorber is then heated to release the ethanol vapor. Sensors are utilized that detect ethanol vapor by measuring its effect on the electrical conductance of a heated metal oxide film on a ceramic substrate.

Infrared detection has been used to quantify ethanol concentration in breath for law enforcement purposes, but the instruments used typically have a path length of about 1 meter making them large and bulky. For passive sensing in a vehicle cabin, utilizing this instrument, infrared detection would require a path length on the order of 100 meters. This is impractical for an on-board sensor. Moreover, in the case of requiring a BAC test before vehicle usage, the passive sensing systems require an extended collection time for collection of vehicle cabin air that is also diluted air.

SUMMARY OF THE INVENTION

A chemical vapor sensor is provided that can actively and passively measure a chemical species of interest with high sensitivity and chemical specificity in a selected area, for use in safety systems. In an embodiment, the present invention provides for optical detection of ethanol for use in motor vehicle safety systems. A practical sized on-board sensor is provided having a passive measurement mode and an active breathalyzer measurement mode.

In an embodiment, ethanol vapor in a vehicle cabin is passively measured and if a predetermined ethanol level is measured, a countermeasure is invoked that involves vehicle occupant action to improve safety. In an embodiment, the active breathalyzer is used as a countermeasure (substitutive or duplicative) to the passive measurement mode. The driver is required to supply a breath sample to the active sensor prior to one or more subsequent vehicle trips, preventing vehicle startup if breath is not supplied or if the measurement test is failed. Alternatively, the breath sample requirement can be imposed for a predetermined time period. In another embodiment, passengers are warned or required to fasten and utilize seat belts if a predetermined ethanol level is measured by the passive measurement mode. Additionally, a combination of the above mentioned countermeasures can be imposed.

Regarding the passive measurement mode, ethanol vapor (and optionally $CO_2$) in a vehicle cabin is measured, and sufficient sensitivity is provided to passively detect a motor vehicle driver (not requiring active involvement by the driver) that exceeds the legal limit of blood alcohol concentration (BAC). At the threshold of intoxication, the concentration of ethanol in breath is legally defined as 0.08 grams of ethanol per 210 liters of breath, which at 1 atmosphere pressure is equivalent to 210 ppm ethanol by volume. The concentration of ethanol in breath is proportional to the BAC of a person. In an embodiment, the present invention provides for passive detection of driver intoxication by employing a passive chemical vapor sensor to measure both ethanol concentration in the range of 0.1 ppm to 10 ppm by volume and $CO_2$ concentration in the vehicle cabin, and using the measurements of ethanol and $CO_2$ to infer the BAC of the driver. Additionally, since drivers can exhibit a BAC of much greater than 0.08, and the vehicle cabin air may be less diluted, the present invention further provides for measuring ethanol concentrations greater than 10 ppm. Alternatively, the present invention passively detects driver intoxication by measuring ethanol vapor in the vehicle cabin and comparing the measured level with a predetermined threshold level. In an embodiment, in comparison to known systems, the present invention increases the sensitivity of detection of ethanol vapor by a factor of about 1,000. Further, the sensor can be situated in an inconspicuous location and operate independently without requiring active involvement by a driver.

Regarding the active breathalyzer measurement mode, ethanol is measured directly from a driver's breath to detect whether the driver exceeds the legal limit of BAC. The breath sample blown is undiluted and, as discussed above, the necessary detection level is about 210 ppm of ethanol. Further, the active breathalyzer measurement mode can resolve ambiguity as to whether an exceeded BAC of ethanol measured by the passive measurement is due to intoxicated passenger(s), rather than an intoxicated driver.

If a predetermined concentration of a chemical species is exceeded, as measured by the passive chemical sensor, the safety system requires that a vehicle occupant perform an action that increases safety. As an example, the safety system can include setting an ethanol flag to a failure setting and preventing the vehicle engine from restarting until the ethanol flag setting is reset to a pass setting as measured by the active breathalyzer. The safety system can require an active breathalyzer test for a predetermined number of vehicle trips and/or it can require the active breathalyzer test for a predetermined time period. In particular, to minimize time inconvenience to a driver in the case of a safety system preventing vehicle starting, the passive measurement mode can be bypassed, and the ethanol detector used for the passive measurement mode can be used for a quick breathalyzer measurement. The safety response can further impose requirements including requiring minimum headway distance behind a preceding vehicle, as well as constrain vehicle performance. Additionally, the safety response can include warning passengers to fasten seat belts.

In regard to the passive measurement mode, features of the invention are achieved in part by increasing the sensitivity of detection of a chemical vapor. A vapor concentrator is utilized to amplify chemical vapor concentration to a detectible level for use with an infrared (IR) detector. In the case of detecting ethanol, air is passed through an adsorber for a predetermined time to collect ethanol vapor. The air flow is stopped and the adsorber is heated to release a higher concentration of ethanol vapor into an IR absorption cell. The ethanol concentration is amplified by about two orders of magnitude due to heating the adsorber. Infrared transmission by an IR source to an IR detector is used to detect the ethanol. An IR filter limits IR detector response to a band that is absorbed by ethanol vapor. Additionally, a microcontroller instructs and carries out an appropriate safety system response if a predetermined concentration of a chemical species is exceeded.

A single channel of infrared detection is utilized, and consequently the present invention is less costly to implement. Further, since a reference channel is made unnecessary, spurious infrared absorption at the infrared wavelength of the reference channel is not a concern. Additionally, when measuring a chemical species, time resolution is not limited by the thermal time constant of the IR source, resulting in a simplified system having improved performance.

In regard to the active breathalyzer measurement mode, features of the invention are achieved in part by passing a breath sample directly into an IR absorption cell (rather than through an absorber as in the case of the passive measurement mode). Like the passive measurement mode, however, infrared transmission by an IR source to an IR detector is used to detect the ethanol. An IR filter limits IR detector response to a band that is absorbed by ethanol vapor. Again, the microcontroller instructs and carries out an appropriate safety system response if a predetermined concentration of a chemical species is exceeded.

Other features and advantages of this invention will be apparent to a person of skill in the art who studies the invention disclosure. Therefore, the scope of the invention will be better understood by reference to an example of an embodiment, given with respect to the following figures.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

Figure 1:
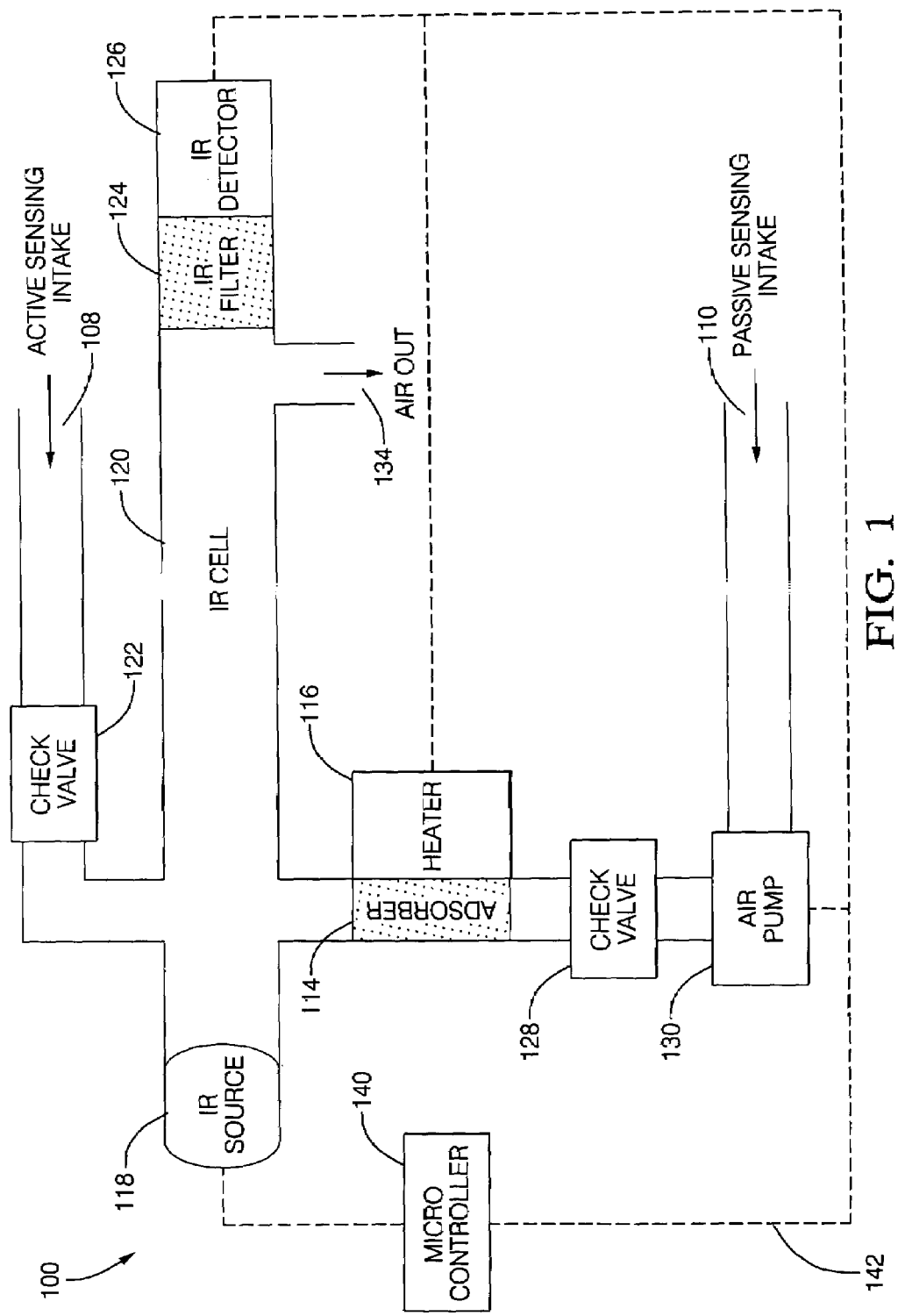
FIG. 1 is a diagrammatic sectional view of components of a chemical sensor including an active sampling tube, passive sampling tube, vapor concentrator and microcontroller, in accordance with an embodiment of the present invention.

1, where concentrated sample vapor is held in an infrared absorption cell for a predetermined and desired time, in accordance with an embodiment of the present invention;

FIGS. 7A, 7B and 7C is a diagrammatic view showing alternative placement/mounting options of the passive sensing intake in a vehicle cabin for the chemical sensor as in FIG. 1, in accordance with an embodiment of the present invention; and FIGS. 8A and 8B is a diagrammatic view showing alternative placement options of an active sensing intake for the chemical sensor as in FIG. 1, in accordance with an embodiment of the present invention.

DETAILED DESCRIPTION OF THE INVENTION

Exemplary embodiments are described with reference to specific configurations. Those of ordinary skill in the art will appreciate that various changes and modifications can be made while remaining within the scope of the appended claims. Additionally, well-known elements, devices, components, methods, process steps and the like may not be set forth in detail in order to avoid obscuring the invention. Further, unless indicated to the contrary, the numerical values set forth in the following specification and claims are approximations that may vary depending upon the desired characteristics sought to be obtained by the present invention.

Presently, in the United States, a driver is legally deemed intoxicated when exhibiting a blood alcohol concentration (BAC) of 0.08%, and therefore violating the law if operating a motor vehicle while intoxicated. Passively monitoring a motor vehicle driver's BAC can facilitate avoiding motor vehicle accidents caused by intoxicated drivers. The BAC measurement can be utilized to instruct a vehicle to shut down or compensate for the effect of BAC on the driver's reaction time. Passive monitoring (rather than active) senses the vehicle driver's BAC without active involvement of the vehicle driver. However, conventional ethanol vapor sensors are unsuitable for on-board passive detection of drunk drivers in regard to monitoring ethanol concentration in the air of a vehicle cabin. Additionally, actively monitoring a motor vehicle driver's BAC can facilitate preventing intoxicated persons from even operating motor vehicles.

A vapor sensor based on infrared transmission requires an appropriate path length. If the path length is too short, the change in detected intensity is small relative to the fluctuations in detected intensity. If the path length is too long, the detected intensity at the center of an absorption line is small. The optimum path length depends upon the chemical concentration that is to be measured. Consider, for example, a sensor that measures the fraction of light transmitted in a fixed band of optical frequency. For improved accuracy the species of interest should maintain on the order of 10% absorption in the band. In conventional chemical sensors, an absorption band near 1070 $cm^{-1}$ (9.4 μm wavelength) is typically used to detect ethanol vapor. Near the peak of the 1070 $cm^{-1}$ band, the absorption coefficient is about $2.5 \times 10^{-4}$ $(\mu mol/mol)^{-1}$ $m^{-1}$. Consequently, with an ethanol concentration of 250 ppm, a path length of 0.7 m is needed to obtain 10% absorption. At the threshold of intoxication, the concentration of ethanol in breath is about 210 ppm (by volume) with 1 atmosphere total pressure. For comparison, to determine the concentration of ethanol vapor in a breath sample, law enforcement typically uses an infrared-based instrument that has a 1 m path length through the breath sample.

However, for passive monitoring of ethanol, vehicle cabin air is monitored (rather than direct monitoring of a driver's breath) and an ethanol sensor consequently requires the ability to monitor a significantly reduced ethanol concentration. As further detailed below, to detect a driver with a BAC near the threshold of legal intoxication, an ethanol sensor employing passive monitoring must be capable of measuring ethanol in the range of 0.1 ppm to 10 ppm in the cabin of a vehicle. Additionally, since drivers can exhibit a BAC of much greater than 0.08, and the vehicle cabin air may be less diluted, a passive ethanol sensor must be capable of measuring ethanol concentrations greater than 10 ppm. If an infrared sensor is to be used to measure an ethanol concentration on the order of 1 ppm, the optimum path length for a commercially available sensor would be on the order of 100 meters (m). It is plainly recognized that the necessity of a 100 m path length limits its use in a vehicle. Thus, commercially available ethanol vapor sensors are too bulky for on-board use, requiring a long pathlength for infrared sensing.

The present invention provides, in part, a vapor concentrator (as further described below) that increases ethanol concentration to a level needed by an infrared (IR) detector for passive detection with vehicle cabin air, and therefore enables the detection of sub-ppm concentrations of ethanol. Further, the present invention improves chemical selectivity.

The following experimental examples are provided for illustrative purposes and are not intended to be limiting.

The ethanol sensitivity needed to passively detect a driver at the threshold of intoxication is additionally determined by the present invention. $CO_2$ that is naturally present in human breath is used as a tracer to determine sensor measurement requirements (sensitivity required) for passive detection of ethanol in a vehicle cabin. This avoids the use of intoxicated human subjects. Ethanol and $CO_2$ do not separate significantly as exhaled breath drifts from a driver's mouth to a location where air is sampled by the passive sensor. The transport of both ethanol vapor and $CO_2$ from a driver's mouth to the sensor is dominated by convection, which is the same for both ethanol and $CO_2$. The concentration of ethanol vapor in breath is proportional to BAC, and is 210 ppm when BAC is 0.08%. The concentration of $CO_2$ in exhaled breath is approximately 36000 ppm (as compared to 370 ppm in ambient air). Like ethanol, $CO_2$ in exhaled breath comes from exchange with blood in the alveolar sacs in the lung. Based on $CO_2$ measurements with a test subject, the breath alcohol concentration at the sensor is at least 0.5 ppm for any HVAC setting (with the windows closed) at 5 minutes after a driver with BAC of 0.08 is seated in the vehicle, and can be as high as 10 ppm and even higher for some vehicles. A number of drivers breathe only half as much air as the test subject, so the ethanol sensor requires sensitivity to 0.2 ppm ethanol in air. Some people have driven with a BAC substantially above the threshold of intoxication, as much as 0.40 and even greater. Further, people that have recently undergone physical exertion can breathe at a volumetric rate by an order of magnitude higher as compared to a test subject person. Therefore, the passive sensor must be capable of measuring ethanol concentration by a factor of 50 or higher than the above-mentioned concentration of 10 ppm.

A system and method is described herein for providing a practical sized on-board sensor having both a passive measurement mode and an active breathalyzer measurement mode.

Referring to the drawings wherein identical reference numerals denote the same elements throughout the various views, FIG. 1 illustrates components of the chemical sensor 100, which includes active sensing intake 108, passive sensing intake 110, a vapor concentrator comprising adsorber 114 and heater 116, and microcontroller 140.

In the case of passive sensing, air is drawn into passive sensing intake 110 by means of air pump 130, passes through check valve 128, adsorber 114 and IR absorption cell 120, and released through air out 134. Air pump 130 is, for example, model TD-3LS from Brailsford and Company, Inc. Check valve 128 is positioned in series to obstruct air flow when air pump 130 is off. Check valve 128 is further useful to prevent flow leakage when active sensing intake 108 is alternatively employed. Adsorber 114 adsorbs ethanol vapor and is heated by heater 116. Adsorber 114 can be comprised of carbon such as carbon molecular sieves, activated carbon, and carbon nanotubes. Alternatively, adsorber 114 can be comprised of a porous organic polymer or an inorganic material having a high surface area such as a zeolite. Adsorber 114 is, for example, a 3 mm long bed of Carboxen 1003 in a glass tube from Supelco. Heater 116 can be constructed by winding resistive wire around a glass tube that encloses adsorber 114, and fastening the resistive wire to the glass tube utilizing epoxy. IR source 118 passes infrared waves across IR absorption cell 120 to IR filter 124, for measurement by IR detector 126. IR source 118 is, for example, an electrical heater, which can be activated by controlling the current. A broad-band emitter such as an Ion Optics source, part number NL5NCC can be employed for IR source 118, when employing a 9.4 micron wavelength band. NL5NCC consists of heated filament (in air) with a calcium fluoride window that separates it from an IR cell. The calcium fluoride window is transparent at this wavelength. Similar devices that emit IR by using electrical power to raise a wire or film to an elevated temperature are available from other manufacturers. When employing a 3.4 micron wavelength band, IR source 118 can also be, for example, an incandescent lamp. IR filter 124 is used to select a range of infrared frequency or wavelength that is adsorbed by ethanol. IR detector 126 can be a thermopile employed to detect IR. The thermopile converts the incident IR into heat and uses a series array of thermocouples to measure the induced temperature rise. IR detector 126 provides an output voltage as a function of time. A microcontroller 140 instructs and coordinates (through signal lines 142) the predetermined operation of chemical sensor 100 components including air pump 130, heater 116, IR source 118 and IR detector 126.

In the case of active sensing, an undiluted sample (such as sample human breath) is forced into active sensing intake 108. The undiluted sample passes through check valve 122, IR absorption cell 120, and is released through air out 134. Check valve 122 is useful to prevent flow leakage when passive sensing intake 110 is alternatively employed. Like passive sensing, IR source 118 passes infrared waves across IR absorption cell 120 to IR filter 124, for measurement by IR detector 126.

The vapor concentrator amplifies the partial pressure of a sample gas, in an embodiment of the present invention. The amplification factor is limited by adsorber's 114 capacity to collect the species of interest. When the limit is exceeded, adsorber 114 begins to saturate, and breakthrough occurs. Let $V_B$ be the volume of sample gas that can be passed through adsorber 114 before breakthrough. Let $V_S$ be the gas volume in adsorber 114. The maximum possible amplification factor is $A=V_B/V_S$. Thus, to optimize A, the breakthrough volume should be maximized relative to the sample volume. One approach is to isolate adsorber 114 as it is heated, for example, by stopping the air flow. As an estimate, the maximum A is the ratio of the breakthrough volume to the volume of adsorber 114 itself. The concentration can alternatively be amplified by rapidly heating adsorber 114 with constant flow of air through the vapor concentrator. If this is done, the maximum concentration depends upon the number of times the air is exchanged while heating, so it is important to heat adsorber 114 rapidly.

The safety consequences of drunk driving result from impaired driving skills and extra risk taking. One approach is to give an impaired driver more time to react. The present invention provides for automatic compensation by a safety system for the slowed reaction time of a drunk driver. For example, if a predetermined concentration of ethanol is exceeded, as measured by the chemical sensor 100 (i.e., an IR sensor), and an ethanol test flag is set to a fail setting, an appropriate safety system response can be carried out by an engine microcontroller 140. The safety system can impose restrictive requirements and limitations including requiring or increasing a minimum headway distance behind a preceding vehicle, as well as constrain vehicle performance. Further, the safety response can warn and require passengers to fasten seat belts. Additionally, the safety system can transmit to police, through a wireless transmitter, a message that indicates a measured ethanol concentration or that the ethanol concentration in the vehicle cabin or the vehicle driver's BAC exceeds a preset level. Further, in an embodiment, in the case of a traffic accident, the safety system can alert an EMS responder or police that ethanol is detected. Additionally, the safety system can transmit any predetermined level of ethanol detection to a flight recorder for downloading by a third party.

Drunk drivers often take risks while driving. The present invention can be used to counter this risk taking by warning the driver of the ethanol measurement and further require the driver and any passengers to acknowledge the warning. This acknowledgement can issue from a vehicle warning requiring the use of seat belts. It should be noted that only about 27% of drivers with BAC above 0.08 killed in traffic accidents in the U.S. were wearing seat belts according to data released by the National Highway Transportation and Safety Administration. Using a seat belt (in a vehicle that has airbags) decreases the fatality rate in a crash by about 29%. As an example, in a case where a passive ethanol sensor is installed in all cars and light trucks in the U.S., and all occupants are wearing seat belts with an intoxicated driver, the use of seat belts could save about 1,250 lives per year, even with no change in driver risk taking or behavior. However, a change in driver behavior could have an even larger impact since, as mentioned above, in 2003 in the U.S. there were 12,373 deaths in crashes in which a driver had a BAC of at least 0.08.

In an embodiment, the safety response further includes monitoring an ethanol flag for a failure setting and preventing the vehicle engine from restarting for a predetermined number of subsequent vehicle trips or for a predetermined time period unless, prior to a vehicle trip, the active breathalyzer measures a driver's BAC as not being legally intoxicated. The active breathalyzer utilizes the active sensing intake 108. In particular, to minimize time inconvenience to a driver in the case of a safety system preventing vehicle starting, the passive measurement mode can be bypassed, and the IR detector 126 used for the passive measurement mode can be used for a quick breathalyzer measurement. It is to be appreciated that, in another embodiment, the ethanol flag setting can be set or reset to a pass or fail setting as measured during a passive measurement, utilizing the passive sensing intake 110. Further, the active breathalyzer measurement mode can clear any ambiguity as to whether an exceeded BAC of ethanol measured by the passive measurement is due to intoxicated passenger(s), rather than an intoxicated driver.

In an embodiment, the combined passive measurement mode and an active breathalyzer measurement mode system and method avoids forcing all drivers to be inconvenienced at every vehicle start. Further, the need to pass an active ethanol measurement is a discouragement to driving while intoxicated. The ethanol flag can serve to alert others, such as parents of a teenage driver, that the vehicle was possibly driven by an intoxicated driver or that ethanol vapor was detected in the vehicle cabin.

The ethanol detection of the present invention can be employed prior to vehicle startup, and can be performed repetitively during vehicle operation. Repetitive sensing enables the present invention to monitor a driver for previously consumed alcohol that will cause the ethanol concentration in the driver's breath to increase over time, perhaps above the legal limit.

Water can condense inside IR absorption cell 120 if IR absorption cell 120 reaches a particular low temperature. This can potentially cause an error in the detection of a small concentration of a particular chemical vapor from IR transmission since the liquid water on the walls of IR absorption cell 120 can cause the intensity of transmitted IR to decrease. In an embodiment, the present invention provides the following adjustments to chemical sensor 100: IR absorption cell 120 is heated to a temperature above the dew point of the vapor released into it from adsorber 114 or from active sensing intake 108. Alternatively, adsorber 114 (carbon) is heated so it is on the order of 10 degrees Celsius above ambient temperature while the ethanol is being adsorbed. This limits the volume of water adsorbed by adsorber 114 to avoid exceeding the dew point when desorbed vapor is vented into IR absorption cell 120. It may be that carbon can adsorb water if it is close to the dew point. Alternatively, the inside of IR absorption cell 120 is coated with a material that prevents water droplets from nucleating, such as presently existing coatings for vehicle windshields that serve a similar function. Alternatively, the air flow is altered through IR absorption cell 120 so that exhaust from the vapor concentrator flows down the center of IR absorption cell 120, but avoids contacting the cool walls where it can condense. Alternatively, an adsorbent material is utilized that is more hydrophobic than carbon, but still adsorbs ethanol vapor.

Figure 2:
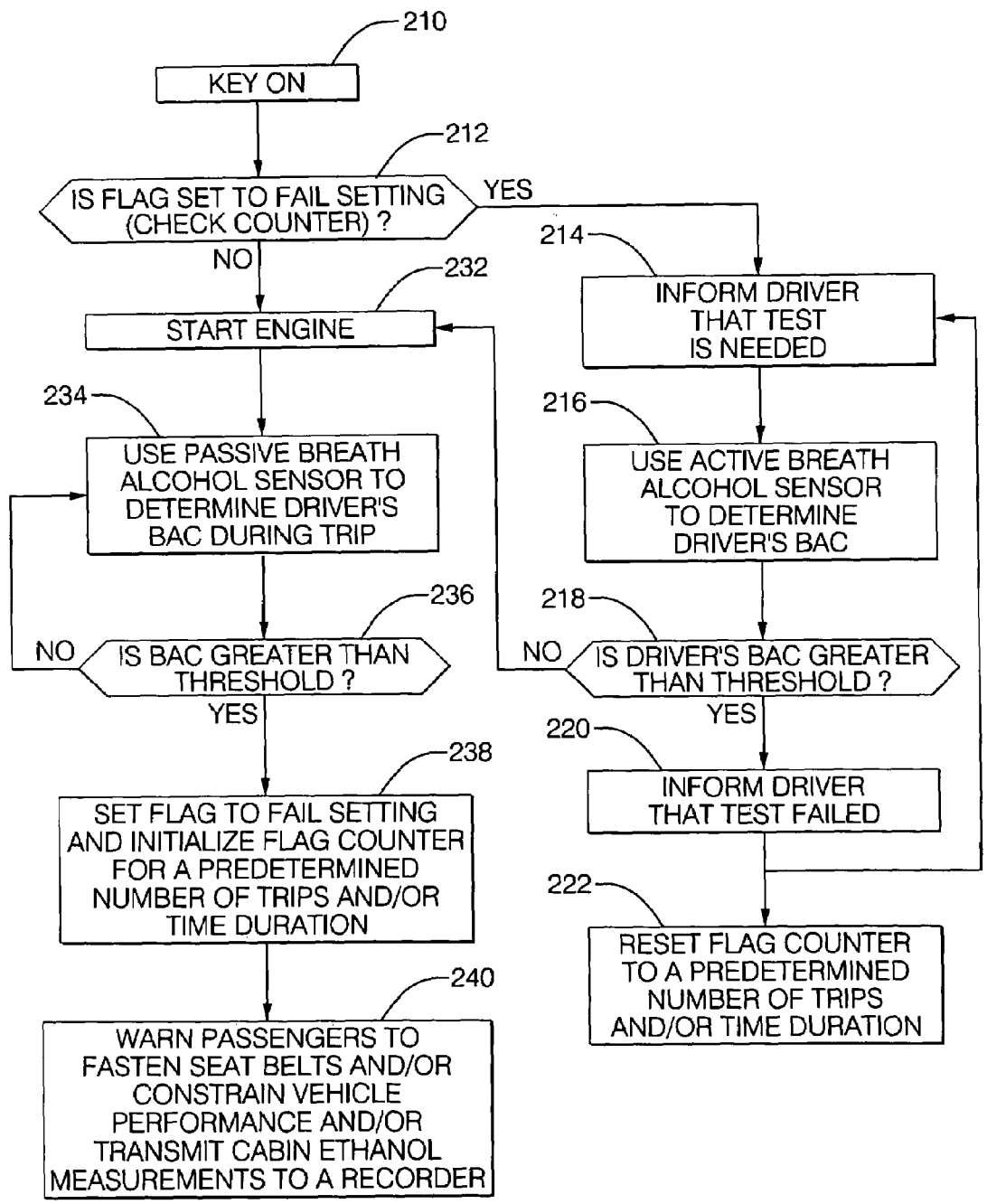
FIG. 2 is a logic diagram illustration of the active and passive measurement of ethanol vapor by the chemical sensor of FIG. 1, in accordance with an embodiment of the present invention.

FIG. 2 is a logic diagram illustration of the active and passive measurement of ethanol vapor by chemical sensor 100. In an embodiment, microcontroller 140 instructs and coordinates the operation of chemical sensor 100 components including air pump 130, heater 116, IR source 118 and IR detector 126. Microcontroller 140 further sets or resets an ethanol measurement flag to a pass setting or fail setting, based on measured ethanol, utilizing active sensing intake 108 and passive sensing intake 110. Microcontroller 140 also checks for a pass setting and a fail setting of the ethanol flag. It is to be appreciated that microcontroller 140 can alternatively check for the absence of a pass setting or fail setting.

Logic box 210 represents the time when a driver intends to start and operate a motor vehicle. At this time the driver inserts a key into the vehicle to start the engine. Decision box 212 represents a decision based upon whether the ethanol flag is set to a fail setting (or does not show a pass setting), in which a counter is checked to determine whether a predetermined number of trips have elapsed or whether a predetermined time has elapsed since the ethanol flag was previously set. This decision can also be made based upon whether both a predetermined number of trips have elapsed and a predetermined time has elapsed. If decision box 212 is determined as being negative, then the flag counter has expired and the engine is permitted to start (logic box 232). If decision box 212 is determined as being affirmative, then the driver is informed that a test is needed to start the vehicle (logic box 214). The vehicle driver then utilizes the active sensing intake 108 to measure the driver's current BAC (logic box 216). If the driver's measured BAC is equal to or greater than the legal BAC limit (decision box 218), then the driver is informed that the ethanol test registers a fail setting (logic box 220). Additionally, the flag counter is reset to a predetermined number of trips or for a predetermined time duration, or both (logic box 222). Further, the diver is given the option to repeat the active test in order to start the vehicle (logic box 214). If the driver's measured BAC is less than the legal BAC limit (decision box 218), then the vehicle engine is permitted to start (logic box 232).

During operation of the motor vehicle, passive ethanol sensing of the vehicle cabin air is performed (logic box 234), employing passive sensing intake 110. This passive sensing is employed to measure a driver's BAC during vehicle operation (decision box 236). If, during the vehicle operation, the passive sensing measures a BAC that is equal to or exceeds the legal limit, the ethanol flag is set to a fail setting and the flag counter is initialized for a predetermined number of trips or for a predetermined time period, or both (logic box 238). As discussed above, when the ethanol flag is set to a fail setting then a safety system response ensues. In an embodiment, if the passive sensing sets the flag to a fail setting (or not to a pass setting) at any time during the vehicle operation, then passengers are warned to fasten safety belts or vehicle performance is constrained or cabin ethanol measurements are transmitted to police, or all are performed (logic box 240). The subsequent vehicle operator is alerted that an active ethanol test is needed prior to vehicle usage, since a BAC concentration of ethanol beyond the legal limit was measured during the previous vehicle trip. Alternatively, if, during vehicle operation, the passive sensing measures a BAC that is less than the legal limit of intoxication, the passive sensing measurement is repeated during vehicle operation.

Figure 3:
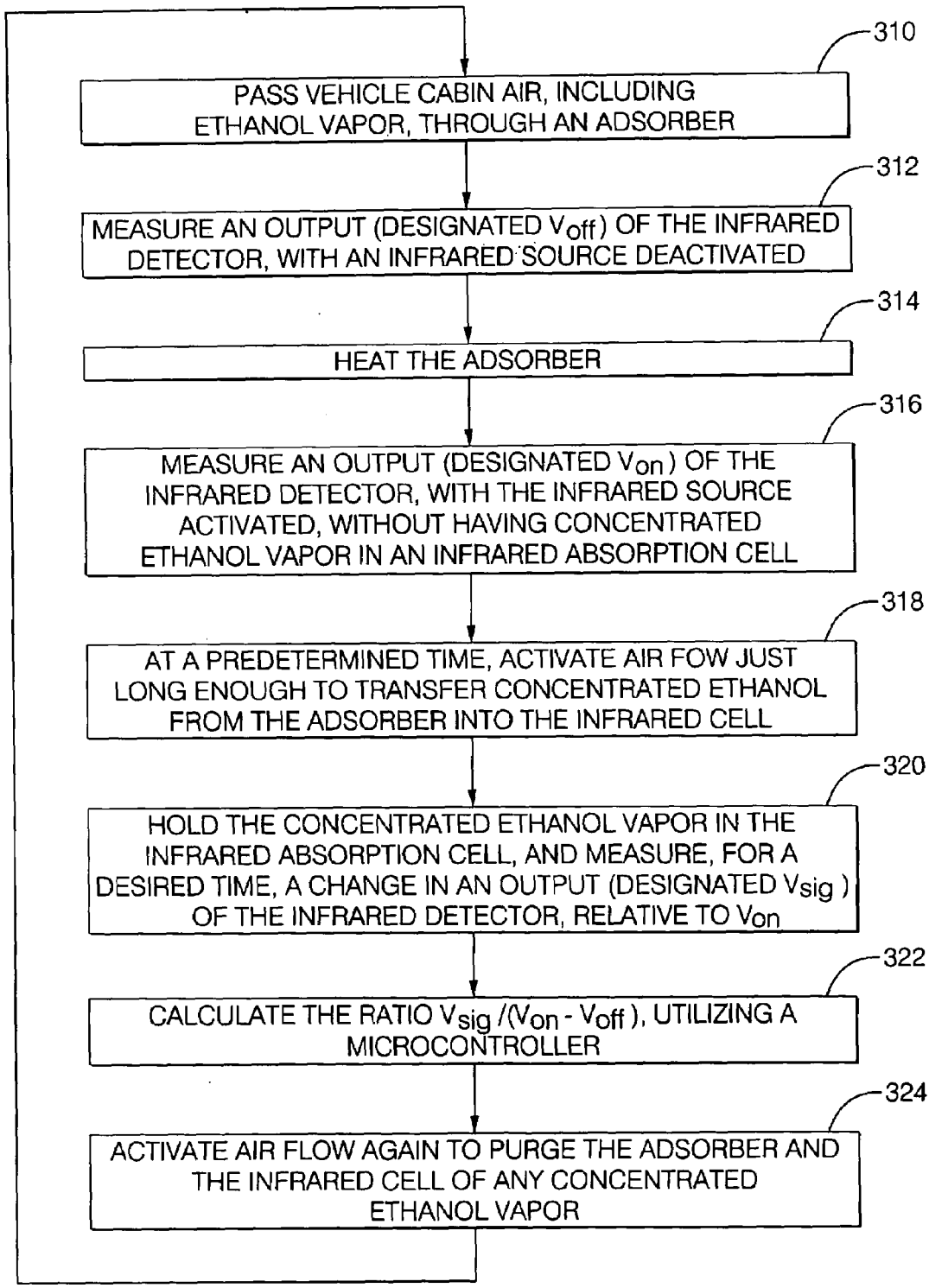
FIG. 3 is a method step illustration of the passive measurement of ethanol vapor with high sensitivity and chemical specificity, in accordance with an embodiment of the present invention.

FIG. 3 is a method step illustration of the passive measurement of ethanol vapor with high sensitivity and chemical specificity. Ethanol vapor is collected by passing ambient air into passive sensing intake 110 and through adsorber 114 (indicated as method step 310). The IR detector 126 provides an output voltage (designated $V_{off}$), with IR source 118 off (indicated as method step 312). The adsorber 114 is heated by heater 116 to release the captured ethanol vapor (indicated as method step 314). The IR source 118 is activated and an output voltage (designated $V_{on}$) of IR detector 126 is measured without having concentrated ethanol vapor in IR absorption cell 120 (indicated as method step 316). At a predetermined time, air flow is activated just long enough to transfer concentrated ethanol vapor from adsorber 114 into IR absorption cell 120 (indicated as method step 318). In another embodiment, concentrated ethanol vapor is passed from adsorber 114 into and through IR absorption cell 120 at a predetermined time. Next, the change in output voltage (designated $V_{sig}$) of IR detector 126 caused by the additional infrared adsorption, relative to $V_{on}$, is measured (indicated as method step 320). As the concentration of ethanol vapor in IR absorption cell 120 increases, there is a decrease in the IR intensity that is detected. Microcontroller 140 calculates the ratio $V_{sig}/(V_{on}-V_{off})$ (indicated as method step 322). By activating the air flow just long enough to transfer concentrated ethanol vapor from adsorber 144 into IR absorption cell 120, the IR transmission can be measured for a predetermined or long period of time. Air flow is activated again to purge adsorber 114 and IR absorption cell 120 of any concentrated ethanol vapor (indicated as method step 324).

A further understanding of the above description can be obtained by reference to the following experimental result examples that are provided for illustrative purposes and are not intended to be limiting.

Figure 4:
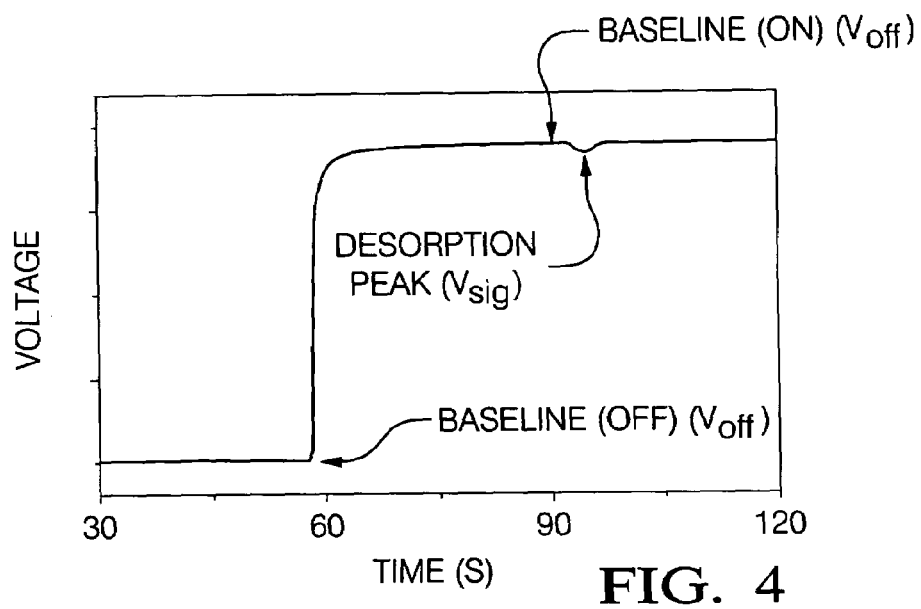
FIG. 4 is a graphical illustration of an example measured voltage as a function of time from the IR detector as in FIG. 1, in accordance with an embodiment of the present invention.

Referring to FIG. 4, a graphical illustration is presented of an example measured voltage as a function of time from IR detector 126 as in FIG. 1. In this example, chemical sensor 100 is sensitive to ethanol and utilizes the passive measurement method steps as described above (where ethanol vapor is passed from adsorber 114 into and through IR absorption cell 120). As indicated in FIG. 4, "baseline off" extends to about 58 seconds, and then a rise in voltage is observed. "Baseline off" corresponds to the time that IR detector 126 provides a measured output (designated $V_{off}$), with IR source 118 off. At about 58 seconds, IR source 118 is activated. At about 90 seconds, the output of IR source 118 substantially levels off having air in the IR cell absorption cell 120, as indicated as "baseline on." The output from IR detector 126 at this time is designated $V_{on}$. With IR source 118 on, at a predetermined time, concentrated ethanol vapor is passed from adsorber 114 into and through IR absorption cell 120, and a dip in IR transmission is observed. The dip in output from IR detector 126 is indicated as "desorption peak." The change in IR detector 126 output (designated $V_{sig}$) is caused by the additional infrared adsorption that occurs, relative to $V_{on}$.

For a sensor that utilizes IR adsorption to determine ethanol concentration, it is desirable that the output be the ratio of two measured quantities. Such a ratio eliminates the gradual drift in calibration that can occur in response to changes such as aging of the light source or accumulation of material that absorbs infrared on the optics. The chemical sensor 100 output provided by the present invention is a ratio. The numerator of the ratio is the integrated "desorption peak" versus time (relative to "baseline on"). The denominator is the difference between "baseline on" and "baseline off."

It is to be appreciated that a single channel of IR detection is employed by the present invention, and consequently the chemical sensor 100 is less costly to implement. Further, since a reference channel is made unnecessary, spurious infrared absorption at the IR wavelength of the reference channel is not a concern. Additionally, when measuring a chemical species, time resolution is not limited by the thermal time constant of IR source 118, resulting in a simplified system having improved performance.

Figure 5:
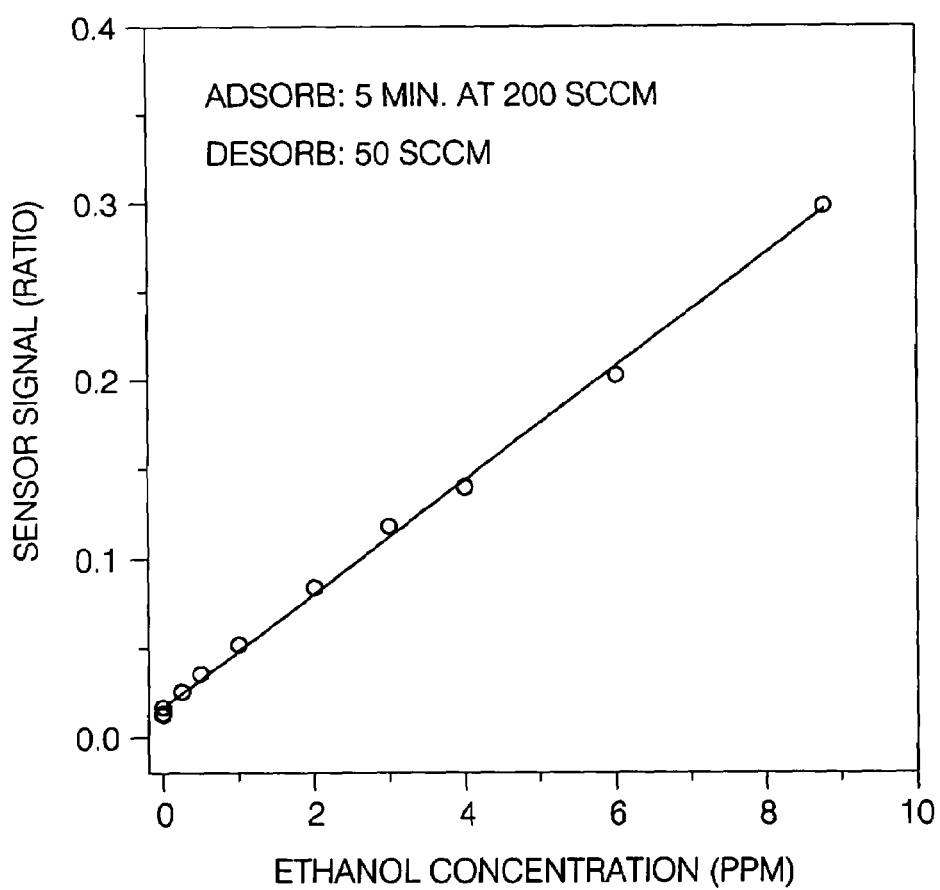
FIG. 5 is a graphical illustration of an example measured IR sensor signal ratio versus ethanol concentration, in accordance with an embodiment of the present invention.

FIG. 5 is a graphical illustration of an example measured IR sensor signal ratio versus ethanol concentration obtained utilizing the method steps as described above (where ethanol vapor is passed from adsorber 114 into and through IR absorption cell 120). As indicated on FIG. 5, ethanol vapor is collected by passing ambient air into and through adsorber 114 for 5 minutes at 200 sccm (standard cubic centimeter per minute). The flow is stopped while adsorber 114 is heated. Then, concentrated ethanol vapor is passed from adsorber 114 into and through IR absorption cell 120 at 50 sccm. This process is more fully described above with reference to FIG. 3.

Data was collected with known ethanol concentrations in the range of 0 to 9 ppm. This ethanol concentration range was selected for experiment since, as discussed above, an experiment to determine ethanol concentration produced by a driver with 0.08 BAC found that five minutes after the driver entered the vehicle, the ethanol concentration in air in the vehicle cabin ranged from about 0.5 ppm to 9.8 ppm. The data was used to obtain a best-fit linear function of known ethanol concentration as a function of chemical sensor 100 output. In this example, the data showed that ethanol concentration was measured with a residual standard error of 0.13 ppm. The chemical sensor 100 (as in FIG. 1), with regard to passive measurement, satisfactorily measures ethanol concentration in the range of 0.1 ppm to 10 ppm, and therefore provides sufficient sensitivity for passive detection of an intoxicated vehicle driver with BAC near the threshold of legal intoxication. Additionally, since drivers can exhibit a BAC of much greater than 0.08, and the vehicle cabin air may be less diluted, the present invention further provides for measuring ethanol concentrations greater than 10 ppm.

Figure 6:
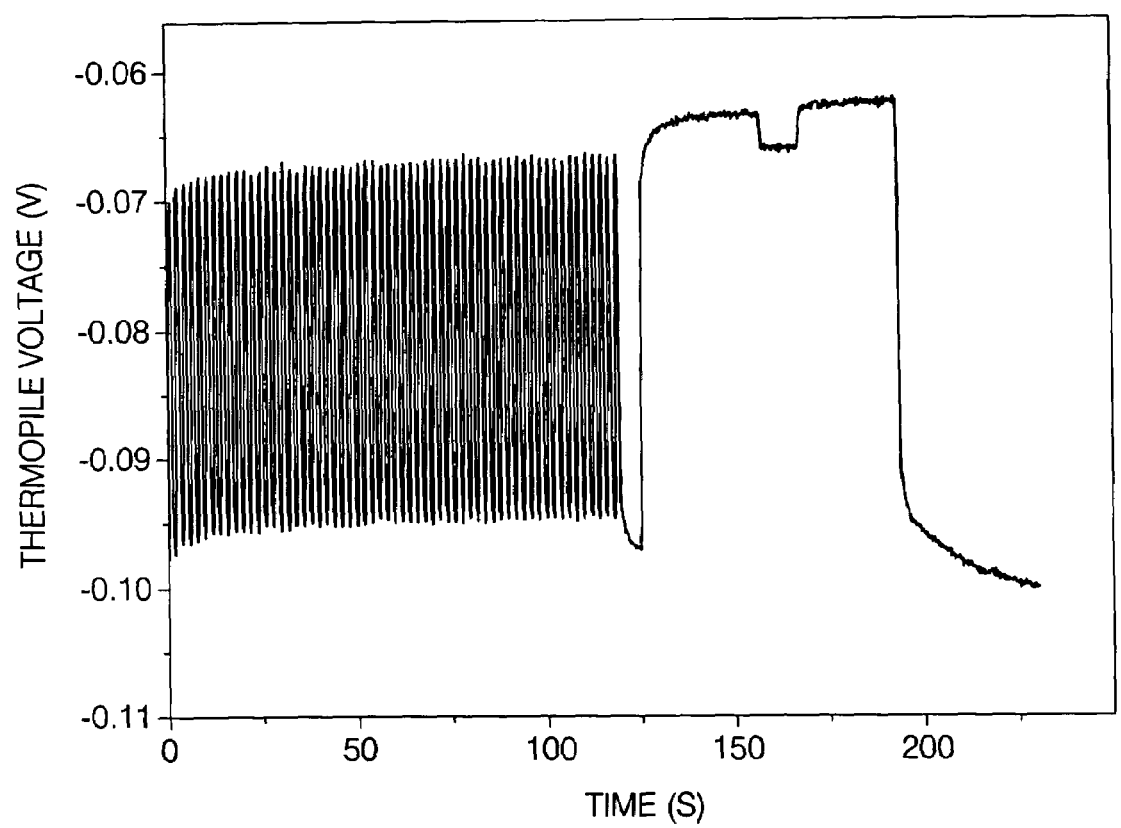
FIG. 6 is a graphical illustration of an example measured voltage as a function of time from the IR detector as in FIG.

Referring to FIG. 6, a graphical illustration is presented of an example measured voltage as a function of time from the IR detector 126 as in FIG. 1. The chemical sensor 100 is sensitive to ethanol, utilizing the method steps as in FIG. 3 (where air flow is activated just long enough to transfer concentrated ethanol vapor from adsorber 114 into IR absorption cell 120). In this particular example, the ethanol concentration in the air is 4.3 ppm.

$CO_2$ is also measured by pulsing IR source 118 on and off as air is passed through adsorber 114 and IR absorption cell 120. $CO_2$ is not adsorbed by adsorber 114. The resulting effect of this pulsing can be observed from about time=0 to time=120, as the voltage jumps to about −0.068 V. Next (as more fully described in FIG. 3), IR source 118 is turned off for about 5 seconds to obtain a "baseline off" value. Subsequently, IR source 118 is activated and adsorber 114 is heated for a predetermined time. The IR detector 126 output voltage is elevated to the "baseline on" value. About 3 seconds later, air pump 130 is activated for 0.2 seconds, transferring concentrated ethanol vapor into IR absorption cell 120, causing the IR transmission to decrease to a constant value. This constant decreased IR detector 126 output voltage can be maintained as long as the concentrated ethanol vapor remains in IR absorption cell 120, as desired. Next, air pump 130 is activated purging adsorber 114 and IR absorption cell 120 of concentrated ethanol vapor. The IR detector 126 output voltage returns to its elevated "baseline on" value. Subsequently, at about 195 seconds, the IR source 118 is turned off and the IR detector 126 output voltage drops. Again, it is to be appreciated that the time periods described in FIG. 6, as well as other time periods described herein, are provided for illustrative purposes and are not intended to be limiting. Other time periods can be employed.

A person with ethanol in their blood tends to evaporate ethanol vapor from their skin into fresh air. Ethanol leaves the body through the skin in two ways. Ethanol in the blood can diffuse through the skin to directly enter the air as ethanol vapor. Additionally, under some circumstances, liquid sweat is formed. Liquid sweat contains ethanol at the same concentration as blood. Ethanol in sweat evaporates to form ethanol vapor in the air. However, the fraction of ingested alcohol that escapes through the skin is only about 1%, so it does not have a significant effect on the average concentration of ethanol vapor in a vehicle cabin. For these reasons, and more, the placement of passive sensing intake 110 is important to more reliable ethanol concentration measurements.

Figure 7:
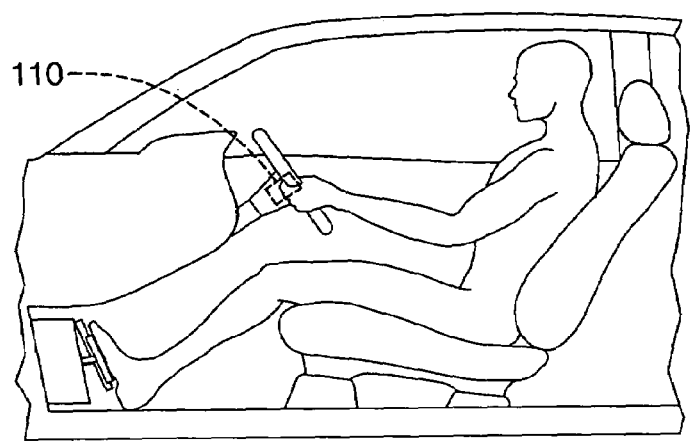
Figure 7:
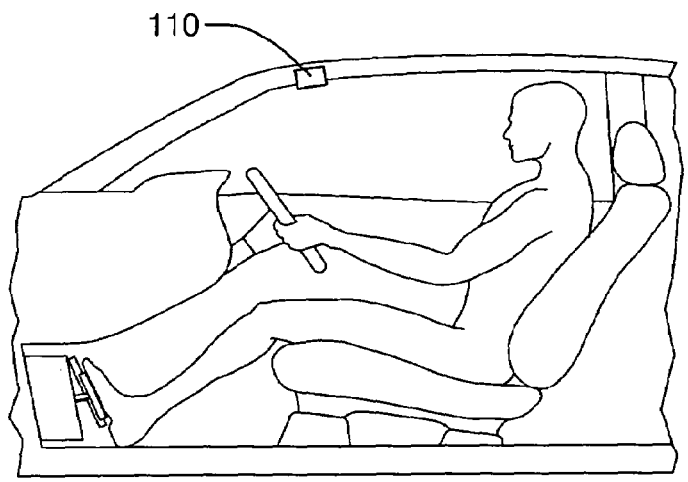
Figure 7:
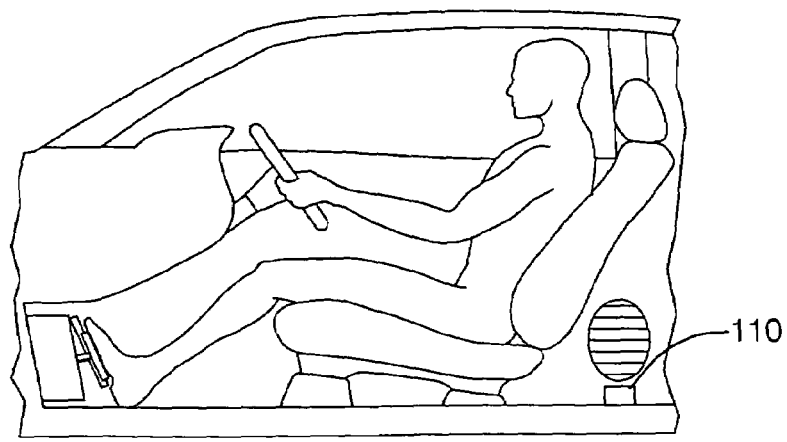

As illustrated in FIG. 7, the present invention provides alternative placement/mounting options of the passive sensing intake 110 in a vehicle cabin for the chemical sensor 100 as in FIG. 1.

It is important to note that exhaled breath from a vehicle driver is mixed with and diluted with air as it drifts to the ethanol sampling location (passive sensing intake 110). The dilution factor depends upon variables such as the speed of the fan blowing fresh air into the cabin, vehicle speed, the settings and directions of the air vents, and the location of the driver's mouth relative to the ethanol sensor. In a simple approximation, breath and air are fully mixed in the cabin before they arrive at the ethanol sensor. An adult male driver typically exhales 10.8 L/min; an adult female driver 9.0 L/min. The maximum air flow from the HVAC (heat-ventilation and air-conditioning) system into a vehicle is typically 250 to 300 cfm (7.08 to $8.50 \times 10^3$ L/min). This suggests that in steady state, the dilution factor could be as low as $1.3 \times 10^{-3}$, and that a passive ethanol sensor should be capable of measuring ethanol vapor concentrations as low as 0.3 ppm. Further, the volumetric breathing rate varies from person to person and is related to physical exertion. The volumetric breathing rate of a subject person must be accounted for to determine the minimum ethanol concentration that is needed for detection.

The vehicle driver's BAC is measured by sensing the concentrations of ethanol vapor in air sampled near the driver. The present invention can measure ethanol vapor concentration at one or more location in the vehicle cabin by placement of passive sensing intake 110 in one or more vehicle cabin locations. Further, the chemical sensor 100 can be situated in an inconspicuous location and operate independently without requiring active involvement by a driver.

For maximized passive ethanol sensitivity to the vehicle driver, it is preferable for the sensor to be exposed to the driver's breath before the driver's breath completely mixes with cabin air. Additionally, since a driver and a number of passengers may be present in the vehicle cabin, in an embodiment of the present invention, passive sensing intake 110 is situated directly adjacent to a vehicle driver. For example, as shown in FIG. 7A, passive sensing intake 110 is incorporated into the vehicle steering wheel or steering column. Additional passive sensing intake 110 placement locations are shown in FIG. 7B and FIG. 7C. Passive sensing intake 110 as shown in FIG. 7B can be incorporated into the vehicle ceiling or dashboard (preferably distant from an air exhaust vent). Alternatively, passive sensing intake 110 can be incorporated into a vehicle body intake vent as shown in FIG. 7C. Further, passive sensing intake 110 can be incorporated into the vehicle headrest, seat, A pillar or B pillar.

Figure 8:
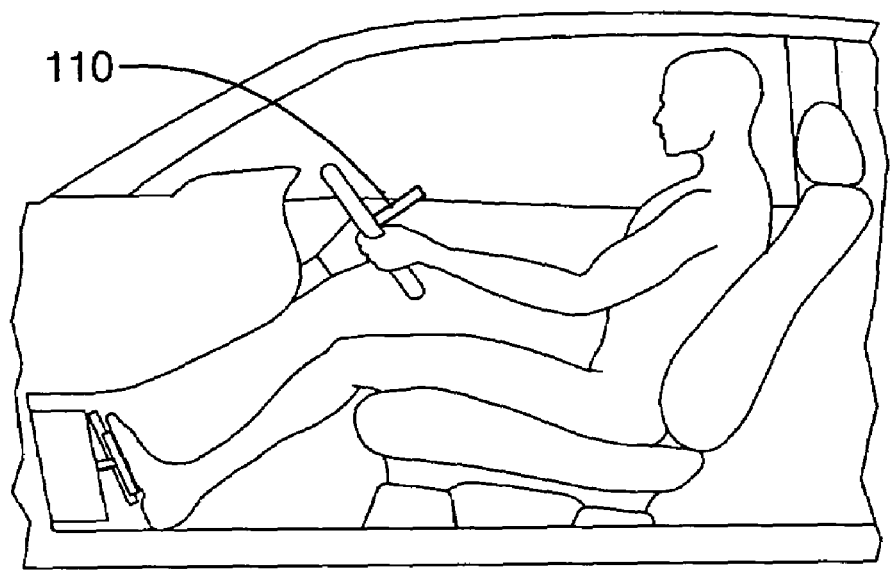
Figure 8:
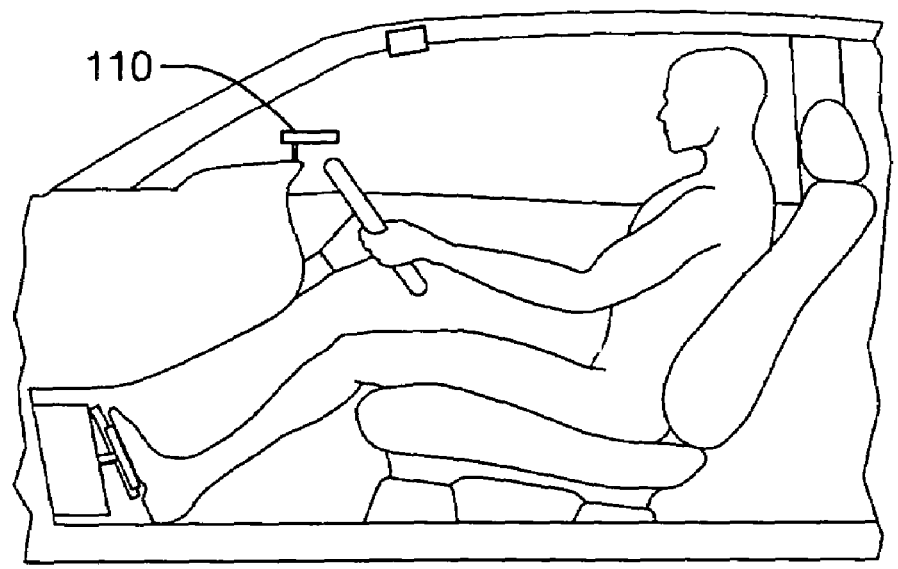

FIG. 8 is a diagrammatic view showing alternative placement options of the active sensing intake 108, for the chemical sensor 100 as in FIG. 1. The present invention can measure ethanol vapor concentration by an active measurement mode taken in a variety of locations in or outside the vehicle cabin. Further, active sensing intake 108 can be situated in an inconspicuous location where, for example, active sensing intake 108 extends and retracts from a position having a concealing cap or cover. Active sensing intake 108 can be situated directly adjacent to a vehicle driver. For example, as shown in FIG. 8A, active sensing intake 108 is incorporated into the vehicle steering wheel or steering column. Additional active sensing intake 108 placement locations are shown in FIG. 8B, mounted on top of, or incorporated into, the dashboard.

Other features and advantages of this invention will be apparent to a person of skill in the art who studies this disclosure. For example, it is to be appreciated that on-board passive ethanol vapor sensors could use a vapor concentrator in conjunction with alternative detection devices including a floating-gate field effect transistor, a gas chromatograph, a heated metal-oxide film sensor, a sensor that measures oxidation luminescence, a CMOS capacitive sensor that uses a polymer film, and a photoacoustic sensor. Further, higher sensitivity is also possible with more elaborate spectroscopic techniques. If a narrow-line laser source is used, its optical frequency can be tuned to one side of a narrow feature in the spectrum, and the laser frequency can be swept back and forth to modulate the transmitted intensity. Sensitivity improves by orders of magnitude if the gas to be analyzed is at a pressure on the order of 1 Pa. Thus, exemplary embodiments, modifications and variations may be made to the disclosed embodiments while remaining within the spirit and scope of the invention as defined by the appended claims.

We claim:

1. A chemical vapor sensor comprising:
   an infrared source for generating infrared waves along a path;
   an infrared detector disposed in said path for receiving the infrared waves and for measuring the intensity of the infrared waves;
   a vapor concentrator including a vapor adsorber adapted for adsorbing a vapor in an air sample and a heating source effective to heat the vapor adsorber to a temperature sufficient to release the vapor therefrom, said adsorber being arranged relative to said path such that the vapor released thereby flows into the path;
   a first sampling intake portion in communication with the vapor adsorber for providing the air sample to the vapor adsorber; and
   a second sampling intake portion in communication with the path for admitting a breath sample into the path.

2. The chemical vapor sensor as in claim 1, further comprising:
   an infrared filter disposed in the path for selecting a range of infrared frequency or wavelength that is adsorbed by the vapor; and
   an infrared absorption cell defining the path and having an inlet for admitting vapors from the vapor adsorber, an inlet for admitting the breath sample and an outlet for expelling gas therefrom.

3. The chemical vapor sensor as in claim 2, further comprising:
   a first flow valve positioned to open when the first sampling intake portion is employed;
   a second flow valve positioned to open when the second sampling intake portion is employed, wherein the first flow valve and the second flow valve open at different times; and
   an air flow source for forcing the air sample from the first sampling intake portion through the vapor adsorber and through the infrared absorption cell.

4. The chemical vapor sensor as in claim 1, wherein the first sampling intake portion is in communication with a motor vehicle cabin, and wherein the infrared detector measures a concentration of ethanol vapor.

5. The chemical vapor sensor as in claim 4, wherein the infrared detector is effective to measure an ethanol concentration in the air sample greater than or equal to 0.1 parts per million (ppm), and measure ethanol concentration in the breath sample of greater than or equal to 150 ppm.

6. The chemical vapor sensor as in claim 4, further comprising a device for instructing a safety response if the ethanol concentration exceeds a predetermined limit, wherein the safety response includes at least one of setting an ethanol flag and setting an ethanol flag counter which requires an active ethanol breathalyzer test for at least one of a predetermined number of vehicle trips and a predetermined time to prevent the vehicle engine from restarting.

7. An ethanol vapor sensor having an active and passive mode for safe vehicle operation comprising:
   an infrared absorption cell defining a path;
   an infrared source for generating infrared waves along the path;
   an infrared detector disposed in said path for receiving infrared waves generated by the infrared source and for measuring the intensity of the infrared waves;
   a vapor concentrator including a vapor adsorber adapted for adsorbing ethanol in an air sample and a heating source effective to heat the vapor adsorber to a temperature sufficient to release adsorbed ethanol therefrom, said vapor adsorber being connected to the infrared absorption cell for passing released ethanol into the cell,
   a first sampling intake portion for admitting an air sample to the vapor adsorber,
   a second sampling intake portion for admitting a breath sample to the infrared absorption cell.

8. The ethanol vapor sensor as in claim 7, further comprising:
   a first flow valve disposed in the first sampling intake to control air flow therethrough; and
   a second flow valve disposed in the second sampling intake portion to control flow of the breath sample into the infrared absorption cell.

9. The ethanol vapor sensor as in claim 7, wherein the infrared detector is adapted to measure an ethanol concentration in an air sample greater than or equal to 0.1 parts per million (ppm), and measure an ethanol concentration in the breath sample greater than or equal to 150 ppm.

10. The ethanol vapor sensor as in claim 7, further comprising a device for instructing a safety response if the ethanol concentration in an air sample exceeds a predetermined first limit or if the ethanol concentration in a breath sample exceeds a predetermined second limit, wherein the safety response includes at least one of setting an ethanol flag and setting an ethanol flag counter which requires an active ethanol breathalyzer test for at least one of a predetermined number of vehicle trips and a predetermined time to prevent the vehicle engine from restarting.

11. The ethanol vapor sensor as in claim 7, wherein the infrared detector utilizes a single absorption channel for infrared detection.

* * * * *